United States Patent
Addington et al.

(10) Patent No.: US 6,655,376 B2
(45) Date of Patent: Dec. 2, 2003

(54) ASPIRATION SCREENING PROCESS FOR ASSESSING POST SURGERY PATIENT'S RISK FOR PNEUMONIA

(75) Inventors: W. Robert Addington, Indialantic, FL (US); Robert E. Stephens, Parkville, MO (US)

(73) Assignee: Pneumoflex Systems L.L.C., Melbourne, FL (US)

( * ) Notice: Subject to any disclaimer, the term of this patent is extended or adjusted under 35 U.S.C. 154(b) by 0 days.

(21) Appl. No.: 09/442,658

(22) Filed: Nov. 18, 1999

(65) Prior Publication Data

US 2002/0104529 A1 Aug. 8, 2002

Related U.S. Application Data

(62) Division of application No. 09/064,028, filed on Apr. 21, 1998, now Pat. No. 6,004,268.

(51) Int. Cl.$^7$ ............................................. A61M 15/00
(52) U.S. Cl. ........................ 128/200.24; 128/200.14; 128/203.12
(58) Field of Search ................. 128/200.14, 200.16, 128/200.24, 203.12, 205.26

(56) References Cited

U.S. PATENT DOCUMENTS

| | | | | |
|---|---|---|---|---|
| 2,918,917 A | * | 12/1959 | Emerson | |
| 3,565,072 A | * | 2/1971 | Gauthier | |
| 3,745,991 A | * | 7/1973 | Gauthier et al. | 600/529 |
| 3,812,854 A | * | 5/1974 | Michaels et al. | 128/200.16 |
| 4,106,503 A | * | 8/1978 | Rosenthal et al. | 128/200.18 |
| 4,257,415 A | * | 3/1981 | Rubin | 128/200.21 |
| 5,233,975 A | * | 8/1993 | Choate | 128/200.14 |
| 5,372,126 A | * | 12/1994 | Blau | 128/200.14 |
| 5,678,563 A | * | 10/1997 | Addington et al. | 600/529 |
| 5,767,068 A | * | 6/1998 | VanDevanter et al. | 514/9 |
| 6,004,268 A | * | 12/1999 | Addington et al. | 600/300 |
| 6,058,932 A | * | 5/2000 | Hughes | 128/200.24 |

* cited by examiner

Primary Examiner—Aaron J. Lewis
(74) Attorney, Agent, or Firm—Allen, Dyer, Doppelt, Milbrath & Gilchrist, P.A.

(57) ABSTRACT

Whether a post surgery intubated patient is at risk for aspiration-based pneumonia is determined by requiring the patient to inhale an aerosol of tartaric acid that will stimulate a sensory innervation of the patient's larynx, if functionally recovered, thereby causing the patient to cough. The resulting cough or lack of cough is graded to determine whether the patient is at risk for pneumonia caused by the aspiration of matter present in the patient's mouth. In a further embodiment, the inability or difficulty of a patient to voluntarily expel potentially threatening fluid and matter from the patient's airway can be remedied by repeated applications of the aerosol chemostimulant spray.

11 Claims, 1 Drawing Sheet

ASPIRATION SCREENING PROCESS FOR ASSESSING POST SURGERY PATIENT'S RISK FOR PNEUMONIA

This is a division of application Ser. No. 09/064,028, filed Apr. 21, 1998 now U.S. Pat. No. 6,004,268.

FIELD OF THE INVENTION

The present invention relates in general to the field of post surgery patient recovery, and is particularly directed to an involuntary cough-based process for determining whether a patient, who has undergone general anesthesia, is at risk for developing aspiration-based pneumonia. This is accomplished by causing the patient to inhale an aerosol chemostimulant that will stimulate a fully functional (recovered) sensory innervation of the patient's larynx, causing the patient to involuntarily cough. If the patient fails to cough, however, it is inferred that the patient's involuntary cough reflex is not yet fully functional, and that the patient is at risk of developing aspiration-based pneumonia.

BACKGROUND OF THE INVENTION

Any patient who is to be given a general anesthetic for a surgical procedure is intubated prior to surgery. Because the anesthetic effectively pharmacologically suppresses brainstem function, inluding a variety of involuntary physiological responses, not the least of which is the ability to cough and clear the upper airway. These brainstem reflexes are suppressed until the anesthetic wears off. Because the tubing that has been inserted into the patient's airway tends to act like a wick—drawing fluid (e.g., secreted saliva) that may be present in the patient's mouth into the patient's airway and lungs—it is critical that the patient's involuntary cough reflex be fully functional at the time the patient is extubated.

Unfortunately, there is currently no mechanism for accurately determining whether or not the patient's ability to involuntarily clear the airway has been fully restored. Instead, because each patient's anesthesia recovery time is different, the standard medical practice is to have a skilled medical practitioner (e.g., anesthesiologist) observe the patient, and then make an 'educated guess' that the patient's anesthetic state has completely subsided, and that it is 'reasonably safe' to extubate the patient, and allow the patient to receive fluids and/or nutrients by mouth. If the patient's involuntary cough reflex is not yet fully restored, however, the patient is at considerable risk of developing pneumonia, as a result of entry into the airway from the patient's mouth of what would otherwise be expelled secretion and/or foreign matter that could be a substrate for breeding bacteria.

In addition, even in those cases where a patient has the ability to cough both involuntarily and voluntarily, the condition of the patient (for example in the case of coronary bypass surgery) may be such that it is extremely difficult and/or painful to have the patient cough voluntarily to clear and expel secretions, mucous and the like from the patient's airway.

SUMMARY OF THE INVENTION

In accordance with a first embodiment of the present invention, the potential problem of post surgery aspiration-based pneumonia, discussed above, is readily determined by means of an aerosol-based screening process, that determines the ability of an extubated post-op recovery patient, whose involuntary cough reflex in the larynx have been previously anesthetized (as by the application of a general anesthetic) or compromised by intubation, to cough involuntarily and thereby clear the patient's airway of secretion and/or foreign matter that could be a substrate for breeding bacteria and cause pneumonia.

For this purpose, the laryngeal cough reflex of the patient is evaluated by introducing (spray-injecting) an aerosol chemostimulant into the patient's mouth, for the purpose of stimulating irritant similar types of receptors in the patient's larynx. The aerosol inhalant preferably comprises that described in U.S. Pat. No. 5,678,563, entitled: "Aspiration Screening Process for Assessing Need for Modified Barium Swallow Study," the disclosure of which is herein incorporated, comprising a nebulized or aerosol solution of tartaric acid (tartrate) mixed with saline and is delivered by a standard aerosol nebulizer.

Although other receptor specific chemostimulants may be employed, studies involving the inhalation of a tartaric acid reveal that inhalation of twenty percent nebulized tartaric acid will stimulate an involuntary and abrupt 'explosive' cough, one hundred percent of the time in those patients whose laryngeal cough reflexes have fully recovered from the anesthetic and are fully functional. Further, tartaric acid is considered to be safe, does not cause pain or discomfort, and has not been shown to cause bronchoconstriction or complications in asthmatics or smokers when inhaled in an aerosol form.

The tartrate-containing aerosol stimulant may be injected into the patient's mouth by a respiratory therapist, using a nebulizer for a relatively brief period of time. The patient may be tested a plurality times at respectively different stimulant strengths to determine whether and at what aerosol strength an involuntary cough can be elicited. During each successive stimulant application, the patient receives progressively increasing concentrations of the aerosol for a prescribed period of time by tidal breathing at one minute intervals using successively increasing percentage concentrations.

If the patient involuntarily coughs as a result of the introduction of any concentration of aerosol stimulant, the inhalation cough test is terminated, regardless of the percentage of concentrations used. The patient's response to the inhalation test is then graded, for example, as a low pneumonia risk (if the patient coughs immediately in response to the initial aerosol spray and the cough appears strong or normal), or as a high pneumonia risk (where the cough appears weak or the patient does not readily cough in response to the initial concentration spray, but requires a more concentrated aerosol application). If the patient fails to cough for any strength of inhaled aerosol stimulant, the inhalation cough test is terminated, and it is determined that anesthetization of the patient's laryngeal cough reflex has not fully subsided, so that the patient remains at high pneumonia risk and may not be given fluids or nutrients by mouth.

In a second embodiment of the invention, using a procedure termed a "pulmonary toilet," involving repeated applications of the tartaric acid aerosol spray described above, the patient is involuntarily forced to cough multiple times and thereby remove potentially threatening fluid and other matter from the patient's airway. This second embodiment of the invention is employed where the condition of the patient is such that it is extremely difficult and/or painful to have the patient cough voluntarily to clear and expel secretions, mucous and the like from the patient's layrnx.

DETAILED DESCRIPTION

Figure 1:
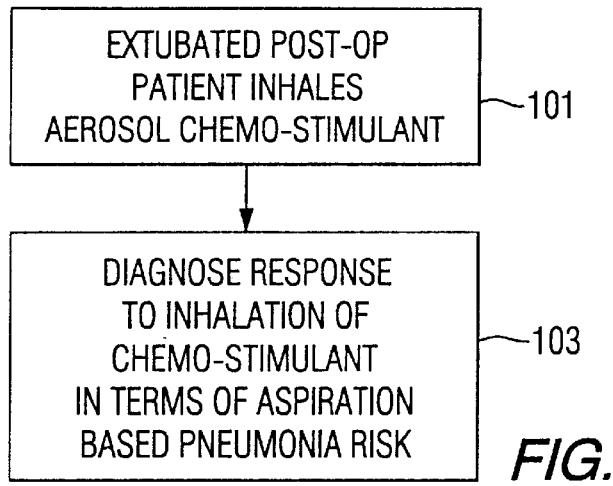
FIG. 1 is a flow diagram of the cough-based screening process for diagnosing whether an extubated post surgery patient is at risk for developing aspiration-based pneumonia in accordance with the present invention.

FIG. 1 is a flow diagram of the steps of the aerosol-based involuntary cough screening process of the present invention for clinically diagnosing whether there is a potential risk for post surgery aspiration-based pneumonia, by introducing (spray-injecting) an aerosol chemostimulant into an extubated patient's mouth, in order to stimulate irritant or similar types receptors in the patient's larynx. During the first step 101, an aerosol chemostimulant is injected into the patient's mouth by a respiratory therapist, using an aerosol inhaler, such as a commercially available Bennett Twin nebulizer, shown at 22 in FIG. 2.

Figure 2:
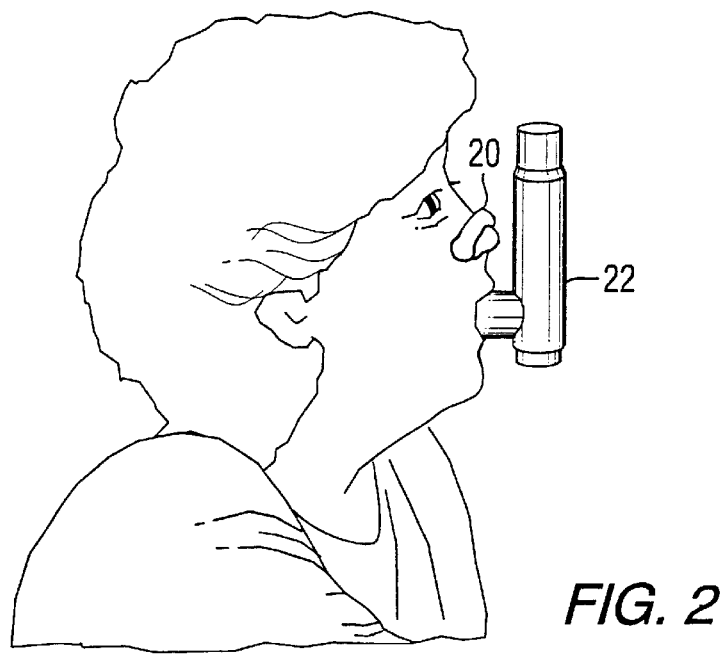
FIG. 2 diagrammatically illustrates the use of an aerosol inhaler in the involuntary cough process of the present invention.

As described briefly above, the aerosol chemostimulant preferably comprises a nebulzed solution of twenty-percent tartaric acid mixed with saline, as described in the above-referenced patent. Although other receptor specific chemostimulants may be employed, studies involving inhaling tartrate, and referenced in the above-identified patent, have shown that tartrate will stimulate an involuntary cough one-hundred percent of the time in normal individuals (i.e. whose laryngeal cough reflexes are functioning normally (not anesthetized)). Moreover, tartrate is considered safe, does not cause pain or discomfort, and has not been shown to cause bronchoconstriction or complications in asthmatics or smokers when inhaled in an aerosol form. During the inhalation cough test, the patient wears a nose-clip 20, as shown in FIG. 2.

The aerosol chemostimulant is preferably inhaled for a prescribed period of time (e.g., on the order of 15 seconds). The nebulizer output spray rate may be on the order of 0.2 ml/min. as a non-limiting example. The patient may be given a plurality of spray applications, up to some prescribed maximum (e.g., three times) at different stimulant strengths, in an effort to elicit a cough. During these successive chemostimulant applications, the patient receives progressively increased concentrations of the aerosol for the prescribed period of time by tidal breathing at one minute intervals using successively increasing percentage concentrations (e.g. 20, 50 and 80 percent).

If, for any aerosol application, the patient involuntarily coughs, the inhalation cough test is terminated, regardless of the percentage of concentrations used. If no involuntary cough is elicited after the maximum number of spray applications and maximum concentration, the test is also terminated. The patient's response to the inhalation test is then graded in STEP 103 as either a low pneumonia risk (as in the case where the patient coughs immediately in response to the initial aerosol spray), or a high pneumonia risk (as in the case where a cough is present but decreased, does not readily cough in response to the initial concentration spray, but requires a more concentrated aerosol application, or does not cough at all).

As pointed out above, should the patient fail to involuntarily cough, irrespective of the strength of inhaled aerosol stimulant, it is determined that anesthetization of the patient's laryngeal cough reflex has not fully subsided, and the patient is diagnosed as remaining at high risk for aspiration-based pneumonia due to a neurologically unprotected airway. This warrants consideration re-intubation, putting the patient on a restricted diet, NPO, or alternative feeding strategies, such as percutaneous endoscopic gastrostomy, until the patient's involuntary cough reflex has completely recovered.

Figure 3:
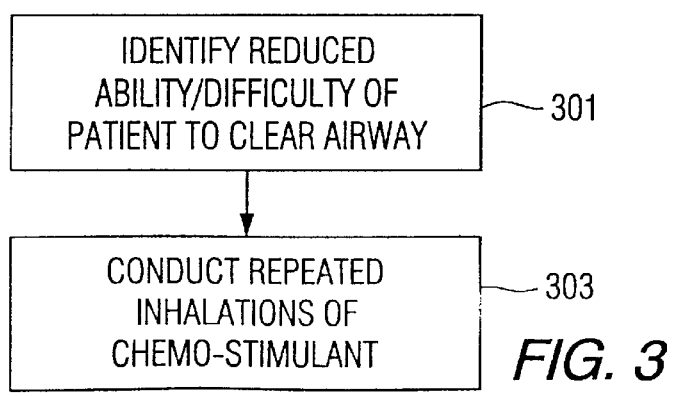
FIG. 3 is a flow diagram of the cough-based therapy process for forcing a patient to clear the patient's airway through repeated applications of a cough reflex stimulating aerosol.

In accordance with a second 'treatment' embodiment of the invention, a flow diagram of which is shown in FIG. 3, the inability of a patient to expel potentially threatening fluid and matter from the patient's airway, identified at step 301, is overcome by repeated applications, as shown by step 303, of an aerosol chemostimulant spray, as described above in the first embodiment. In the second embodiment, the concentration employed is preferably the lowest concentration which is effective to stimulate a cough. As described above, such an inability of the patient to clear and expel secretions, mucous and the like from the patient's larynx may occur in those instances where the condition of the patient is such that it is extremely difficult and/or painful to have the patient cough voluntarily.

The number of aerosol chemostimulant repetitions will depend upon the secretion-expelling response of the patient to each application. After each application, and associated expelling of secretions by the patient, the patient is examined to determine whether an additional application aerosol chemostimulant is required, to clear the airway for that treatment. The patient is continuously monitored and the procedure is repeated at whatever intervals are necessary to maintain the patient's airway free of fluid and secretions that constitute a risk of aspiration-based pneumonia.

As will be appreciated from the foregoing description, whether an extubated post surgery patient is at risk for aspiration-based pneumonia is readily determined in accordance with the present invention, by requiring the patient to inhale an aerosol that will stimulate a fully functional sensory innervation of the patient's larynx, and cause the patient to cough involuntarily. Depending upon the patient's cough response or lack thereof, the patient can be graded to determine whether the patient is at risk for pneumonia. In addition, the inability of a patient to readily expel potentially threatening fluid and matter from the patient's airway can be remedied by repeated applications of the aerosol chemostimulant spray of the first embodiment.

While we have shown and described several embodiments in accordance with the present invention, it is to be understood that the same is not limited thereto but is susceptible to numerous changes and modifications as known to a person skilled in the art, and we therefore do not wish to be limited to the details shown and described herein but intend to cover all such changes and modifications as are obvious to one of ordinary skill in the art.

What is claimed:

1. A method of clearing a patient's airway, comprising repeatedly stimulating a sensory innervation of the larynx by contacting the patient's airway with a composition including a pharmaceutically acceptable carrier and tartaric acid mixed therewith in an amount effective for producing a cough, so as to cause the patient to produce multiple successive coughs until the airway is cleared.

2. Them method of claim 1, wherein the composition contains up to about 80% tartaric acid.

3. The method of claim 1, wherein the composition contains about 20% tartaric acid.

4. The method of claim 1, wherein contacting further comprises repeated contacts with compositions having different concentrations of tartaric acid.

5. The method of claim 1, wherein contacting further comprises successive contacts, each contact including a higher concentration of tartaric acid.

6. The method of claim 1, wherein contacting comprises tidal breathing.

7. The method of claim 1, wherein contacting further comprises an aerosol of said composition.

8. The method of claim 1, wherein contacting comprises repeated contacts by an aerosol of said composition.

9. The method of claim 1, wherein contacting comprises progressively increasing concentrations of said composition in an aerosol.

10. The method of claim 1, wherein contacting comprises progressively increasing concentrations of tartaric acid in an aerosol of said composition.

11. The method of claim 1, wherein the pharmaceutically acceptable carrier comprises saline solution.

* * * * *